(12) United States Patent
Koivisto et al.

(10) Patent No.: US 10,779,770 B2
(45) Date of Patent: Sep. 22, 2020

(54) SEISMOCARDIOGRAPHY

(71) Applicant: Suunto Oy, Vantaa (FI)

(72) Inventors: Tero Koivisto, Turku (FI); Mikko Pänkäälä, Turku (FI); Tapani Nevalainen, Turku (FI); Kati Sairanen, Turku (FI)

(73) Assignee: Suunto Oy, Vantaa (FI)

( * ) Notice: Subject to any disclaimer, the term of this patent is extended or adjusted under 35 U.S.C. 154(b) by 253 days.

(21) Appl. No.: 15/910,079

(22) Filed: Mar. 2, 2018

(65) Prior Publication Data

US 2018/0249962 A1    Sep. 6, 2018

(30) Foreign Application Priority Data

Mar. 3, 2017 (FI) ..................................... 20175199
Mar. 3, 2017 (GB) .................................. 1703458.8

(51) Int. Cl.
*A61B 5/00* (2006.01)
*H03F 3/187* (2006.01)
(Continued)

(52) U.S. Cl.
CPC .......... *A61B 5/7225* (2013.01); *A61B 5/1107* (2013.01); *A61B 5/6823* (2013.01); *A61B 5/7257* (2013.01); *H03F 3/187* (2013.01); *H03F 3/45475* (2013.01); *H03F 3/70* (2013.01); *A61B 2562/0219* (2013.01); *H03F 3/005* (2013.01); *H03F 3/45* (2013.01); *H03F 2200/03* (2013.01);
(Continued)

(58) Field of Classification Search
CPC ... A61B 5/7225; A61B 5/1107; A61B 5/6823; A61B 5/7257; A61B 2562/0219; H03F 3/187; H03F 3/45475; H03F 3/70; H03F 3/005; H03F 3/45; H03F 2200/03; H03F 2200/261; H03F 2203/45138; H03F 2203/45514; H03F 2203/45548
See application file for complete search history.

(56) References Cited

U.S. PATENT DOCUMENTS 6,390,996 B1 * 5/2002 Halperin ............ A61B 5/04017
601/41
2010/0094147 A1    4/2010 Inan et al.
(Continued)

FOREIGN PATENT DOCUMENTS

CN    103308720 A    9/2013
EP     1335185 A1    8/2003
(Continued)

OTHER PUBLICATIONS

Koivisto et al: Automatic detection of atrial fibrillation using MEMS accelerometer. Computing in Cardiology IEEE, 2015, No. 42, pp. 829-832.
(Continued)

*Primary Examiner* — Lindsey G Wehrheim
(74) *Attorney, Agent, or Firm* — Laine IP Oy

(57) ABSTRACT

According to an example aspect of the present invention, there is provided an apparatus comprising two charge amplifiers configured to receive input from an acceleration sensor and to each produce one first output signal, a differential amplifier configured to receive the first output signals and to amplify a difference between the first output signals to produce two second outputs signals.

15 Claims, 7 Drawing Sheets

(51) Int. Cl.
*H03F 3/45* (2006.01)
*H03F 3/70* (2006.01)
*A61B 5/11* (2006.01)
*H03F 3/00* (2006.01)

(52) U.S. Cl.
CPC .................. *H03F 2200/261* (2013.01); *H03F 2203/45138* (2013.01); *H03F 2203/45514* (2013.01); *H03F 2203/45548* (2013.01)

(56) References Cited

U.S. PATENT DOCUMENTS

| | | |
|---|---|---|
| 2013/0338460 A1 | 12/2013 | He et al. |
| 2015/0282768 A1 | 10/2015 | Luna et al. |
| 2015/0311868 A1 | 10/2015 | Wan et al. |
| 2016/0079941 A1 | 3/2016 | Zhong |

FOREIGN PATENT DOCUMENTS

| | | |
|---|---|---|
| JP | 2008259090 A | 10/2008 |
| WO | WO2010145009 A1 | 12/2010 |
| WO | WO2016134936 A1 | 9/2016 |

OTHER PUBLICATIONS

Paukkunen: Seismocardiography: Practicalimplementation and feasibility. AALTO University Publication Series. 2014, ISSN 1799-4942, p. 23, lines 1-14.

\* cited by examiner

SEISMOCARDIOGRAPHY

FIELD

The present invention relates to monitoring of heart activity, such as activity of a human heart.

BACKGROUND

Heart activity may be monitored using various kinds of methods, which include, for example, auscultation, ultrasound examinations and electrocardiography, ECG. Auscultation may comprise listening to sounds generated by the heart, for example using a stethoscope. Different methods are suited to different settings and require differing levels of expertise. In a home setting, an ECG may present itself as a useful option, since it requires only a low level of user expertise.

Performing an ECG measurement involves obtaining an electrical connection with the person's skin, in order to access electrical signals originating from the heart. For example, two electrodes may be used with a separation between them of approximately 5-10 centimetres, to generate ECG sensor data that characterizes heart activity.

Heart data, obtained using ECG or other methods, may be analysed by human experts or automated expert systems, to classify the monitored heart activity as normal or abnormal. In case the activity is classified as abnormal, the abnormality may further be classified, to determine if the heart is in a tachycardia state, a bradycardia state, or a ventricular fibrillation state, for example.

A further method to monitor heart activity is seismocardiography, by which it is meant non-invasive measurement of accelerations in the chest wall produced by myocardial movement. Unlike in ECG, seismocardiography does not require an electrical connection with the person's skin. Rather, an acceleration sensor may be placed on the person's chest, where it generates acceleration sensor data that characterizes heart activity.

Since electrical connection with skin is not required in seismocardiography, it presents as more suitable and convenient for long-duration heart monitoring. On the other hand, acceleration sensor data obtained from an acceleration sensor placed on the person's chest comprises various kinds of unwanted signals generated from the person's movement and breathing, for example.

SUMMARY OF THE INVENTION

The invention is defined by the features of the independent claims. Some specific embodiments are defined in the dependent claims.

According to a first aspect of the present invention, there is provided an apparatus comprising two charge amplifiers configured to receive input from an acceleration sensor and to each produce one first output signal, a differential amplifier configured to receive the first output signals and to amplify a difference between the first output signals to produce two second outputs signals.

Various embodiments of the first aspect may comprise at least one feature from the following bulleted list:
- the second output signals of the differential amplifier are connected, via switches, to leads conveying the first output signals
- when the switches are closed, an output state of the differential amplifier is reset
- the switches are open, off-resistance of the switches forms a resistive feedback and an active high pass filter functionality is generated, the active high pass filter functionality suppressing a constant acceleration component in the input from the acceleration sensor
- the switches are connected in parallel with capacitors
- at least one processing core configured to trigger a measurement state responsive to a determination that motion disturbances are below a threshold
- the at least one processing core is configured to maintain the apparatus in a motion recognition state when the motion disturbances are not below the threshold
- the at least one processing core is configured to, based on the second output signals, determine whether a person the acceleration sensor is measuring is experiencing atrial fibrillation
- a differential analogue to digital converter configured to receive the two second output signals, and to output a digital representation thereof.

According to a second aspect of the present invention, there is provided a method comprising receiving, in two charge amplifiers, input from an acceleration sensor, producing, in each of the charge amplifiers, one first output signal, and amplifying, in a differential amplifier, a difference between the first output signals to produce two second outputs signals.

Various embodiments of the second aspect may comprise at least one feature from the following bulleted list:
- the second output signals of the differential amplifier are connected, via switches, to leads conveying the first output signals
- resetting an output state of the differential amplifier is reset by closing the switches
- when the switches are open, off-resistance of the switches forms a resistive feedback and an active high pass filter functionality is generated, the active high pass filter functionality suppressing a constant acceleration component in the input from the acceleration sensor
- the switches are connected in parallel with capacitors
- triggering, by at least one processing core, a measurement state responsive to a determination that motion disturbances are below a threshold
- maintaining, by the at least one processing core, a motion recognition state when the motion disturbances are not below the threshold
- determining, by the at least one processing core, based on the second output signals, whether a person the acceleration sensor is measuring is experiencing atrial fibrillation
- receiving the two second output signals in a differential analogue to digital converter, outputting a digital representation thereof.

According to a third aspect of the present invention, there is provided an apparatus comprising means for receiving, in two charge amplifiers, input from an acceleration sensor, producing, in each of the charge amplifiers, one first output signal, and amplifying, in a differential amplifier, a difference between the first output signals to produce two second outputs signals.

According to a fourth aspect of the present invention, there is provided a non-transitory computer readable medium having stored thereon a set of computer readable instructions that, when executed by at least one processor, cause an apparatus to at least receive, in two charge amplifiers, input from an acceleration sensor, produce, in each of the charge amplifiers, one first output signal, and amplify, in a differential amplifier, a difference between the first output signals to produce two second outputs signals.

According to a fifth aspect of the present invention, there is provided a computer program configured to cause a method in accordance with the second aspect to be performed.

EMBODIMENTS

A three-amplifier architecture for seismocardiographic acceleration sensor data is described herein, such that one of the three amplifiers is a differential amplifier, arranged to amplify a difference of the outputs of the other two amplifiers. An output of a differential amplifier may be fed to a differential analogue-to-digital converter, which is well suited to seismocardiographic signals, since such signals are noisy and the actual signal characterizing heart activity has a low amplitude. A band-pass filtering function may be generated from a combination of a low-pass filter and an high-pass filtering function arising from a resistive feedback connection over the differential amplifier.

Figure 1:
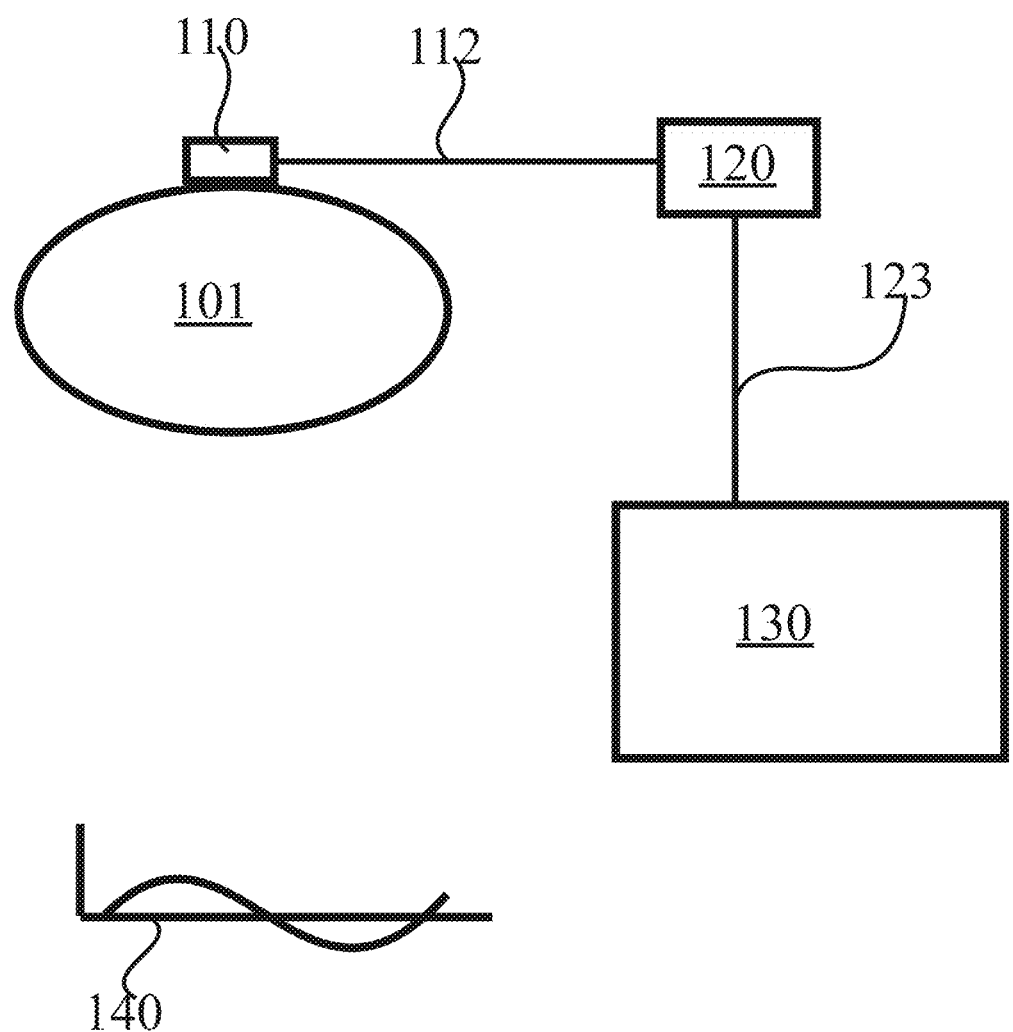
FIG. 1 illustrates an example system in accordance with at least some embodiments of the present invention.

FIG. 1 illustrates an example system in accordance with at least some embodiments of the present invention. A person's chest 101 is schematically illustrated. On the chest is placed an acceleration sensor 110, which generates acceleration sensor data and transmits the generated acceleration sensor data to a readout apparatus 120, via connection 112. Connection 112 may be a wire-line connection or, at least in part, a wireless connection, where applicable. In some embodiments, readout apparatus 120 and acceleration sensor 110 are comprised in a same physical device, in which case connection 112 may be internal to that device, for example.

Readout apparatus 120 may be configured, for example by furnishing it with suitable analogue and/or digital components, to cause the acceleration sensor data originating in acceleration sensor 110 to be processed as it traverses readout apparatus 120. Such processing may comprise filtering, such as band-pass filtering, for example. In principle, bandpass filtering may be performed by a bandpass filter, or by a combination of a lowpass filter and a highpass filter, or, indeed components that effectively perform as a lowpass and/or highpass filter. The acceleration sensor data may be converted into digital form in an analogue-to-digital converter, either in readout apparatus 120 or subsequent to it. A differential analogue-to-digital converter may be employed, for example to convert an output of a differential amplifier comprised in readout apparatus 120 to digital form.

An optional analytics device 130 is further illustrated in FIG. 1, connected to readout apparatus 120 via connection 123. Analytics device 130 may be configured to perform determinations on heart activity based on acceleration sensor data obtained from acceleration sensor 110. For example, analytics device 130 may be configured to determine if the person's heart is in an abnormal state, such as bradycardia, tachycardia or atrial fibrillation, for example. Analytics device 130 may be configured to provide an alarm responsive to a determination the person's heart is in an abnormal state.

Analytics device 130 may be comprised in a server or cloud server farm, for example. Analytics device 130 may store acceleration sensor data, in raw and/or processed form, for future reference. In some embodiments, analytics device 130 is comprised in a same physical device as readout apparatus 120 and/or acceleration sensor 110. For example, a device intended for home use may comprise integrated therein acceleration sensor 110, readout apparatus 120 and analytics device 130. For example, such a device may comprise the acceleration sensor, readout circuitry and a processor or controller configured, by software and/or hardware, to perform analytical determinations on the acceleration sensor data.

Analytics device 130, or another device arranged to perform determinations concerning the acceleration sensor data, may process the acceleration sensor data, for example after it has been filtered and converted to digital format. Processing may comprise Fourier transformations, pulse detection and null-data detections, for example. Processing may be done by software, for example. Fourier transformations may be used to identify frequencies in the sensor data. Pulse detection may be used to identify heartbeats, for example. Null-data detection may be used to identify a condition, where acceleration sensor 110 has become decoupled from chest 101, such that it cannot observe vibrations caused by the person's heart. In case null data is observed, a signal may be provided to the person to correct the placement of acceleration sensor 110, for example.

A seismocardiographic signal may have low frequency, such that the main components may have a frequency of less than 20 Hz. The largest amplitude may be less than 0.05 g, where g is the standard acceleration of the Earth. A suitable seismocardiographic may be obtained by measuring from the thorax toward the back, for example, to obtain a strongest possible signal.

FIG. 1 further has a graph 140 that illustrates output of acceleration sensor 110 as a function of time. In detail, in this graph the horizontal axis corresponds to time, with time advancing from left to right, and the vertical axis corresponds to an acceleration signal voltage obtained from acceleration sensor 110. The illustrated signal may correspond to a motion pulse created by the person's heart, such that an initial positive acceleration signal gives way to a subsequent negative acceleration pulse. The output signal of acceleration sensor 110 may, in general, be an analogue voltage signal, for example.

Figure 2:
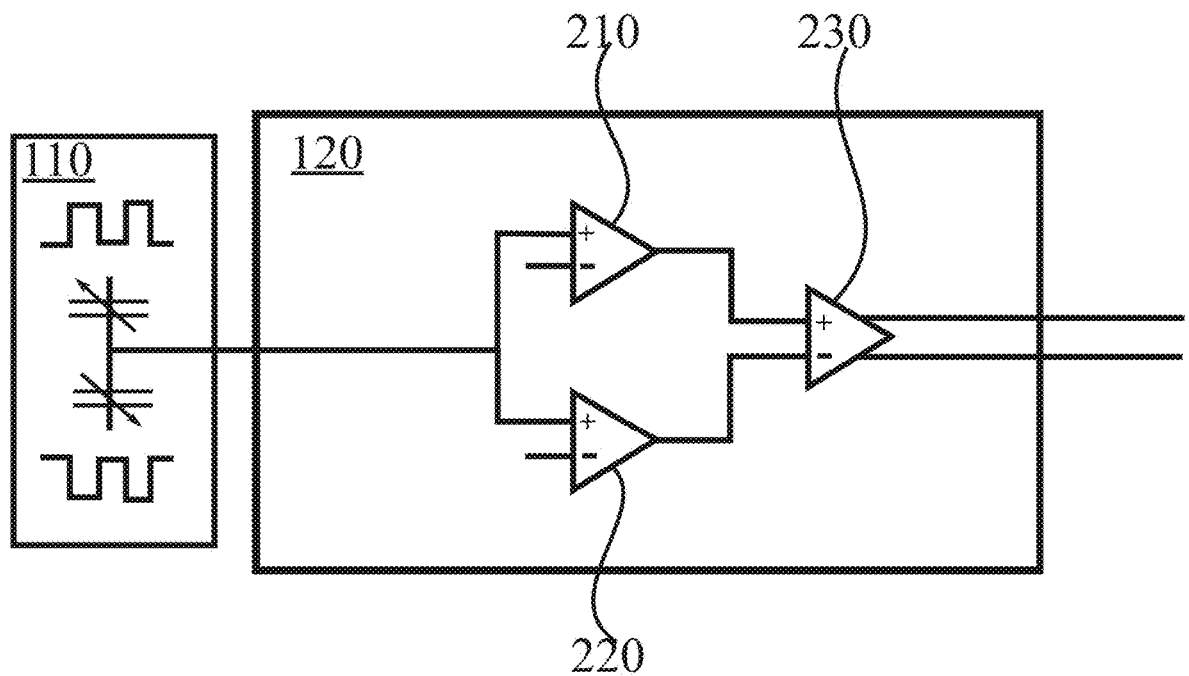
FIG. 2 illustrates an example apparatus in accordance with at least some embodiments of the present invention.

FIG. 2 illustrates an example apparatus in accordance with at least some embodiments of the present invention. Like numbering denotes like structure as in FIG. 1. Acceleration sensor 110 is disposed on the left, with readout apparatus 120 to the right.

Output from acceleration sensor 110 is connected, as illustrated, to first charge amplifier 210 and second charge amplifier 220. For example, first charge amplifier 210 may be configured to amplify a charge pulse caused by a positive acceleration and second charge amplifier 220 may be configured to amplify a charge pulse caused by a negative acceleration.

The outputs of first charge amplifier 210 and second charge amplifier 220 are connected to inputs of a differential amplifier 230. Differential amplifier 230 is configured to amplify a difference between its inputs, that is, to amplify a difference between the outputs of the first and second charge amplifiers 210, 220. Outputs of differential amplifier may be provided to an analogue-to-digital converter, such as, for example, a differential analogue-to-digital converter, ADC.

Accelerometer sensor 110 may consist of two mechanical capacitors connected in series, which change their capacitance according to acceleration pulses. Two actuator signals with 50% duty cycle and opposite phase may be led to the top and bottom plates of the sensor enabling complementary acceleration induced charge pulses to be read at a middle node. Consecutive transition edges of the actuator signals provides positive and negative edge of the acceleration induced charge pulse.

In use, seismocardiographic measurements may be performed, using the system illustrated in FIG. 2, to monitor a heart. The illustrated three-amplifier architecture utilizes the edges of both positive and negative acceleration pulses to increase a level of amplification that is obtained. Further, a differential amplifier provides a benefit in that a differential ADC may be employed. Differential ADCs are less susceptible to noise in input than single-input ADCs. This is beneficial especially in seismocardiography, as seismocardiographic signals are small in amplitude and they may be present with noise.

Low-pass filtering may be employed, for example after the charge amplifiers, to control high-frequency noise. Further, high-pass filtering may also be employed, to control low-frequency components, such as movement of the chest due to breathing, and the standard acceleration of the Earth's gravity, g. Where both low-pass filtering and high-pass filtering are present, the resulting filtering may be considered band-pass filtering.

The system of FIG. 2 may further comprise a processor or processing core, and memory, which may be comprised in the processor or processing core, for example. Thus the apparatus may be enabled to operate in two states, a motion recognition state and a measurement state, for example, under the control of the processor or processing core. A motion recognition state may comprise that heart monitoring is not active, and the apparatus waits until a determination may be made, that motion disturbances are below a threshold. Responsive to the motion disturbances being determined to be below the threshold, the apparatus may switch itself to a measurement state, where heart monitoring is active. Where heart monitoring is done when motion disturbances are below a threshold, a benefit is obtained in that the acceleration sensor data is less noisy and seismocardiographic procedures may proceed with a cleaner signal. In the motion recognition state, a gain factor of the apparatus may be different, for example lower, than in the measurement state. Likewise power consumption of the apparatus is reduced by limiting active heart monitoring to times when motion disturbances are below the threshold.

In general, the processor or processing core may monitor motion disturbances from the acceleration sensor data, either in analogue or digital format. In some embodiments, the processor or processing core is comprised in analytics device 130, rather than in readout apparatus 120, and analytics device 130 is configured to cause readout apparatus 120 to switch between the measurement state and the motion recognition state.

Figure 3:
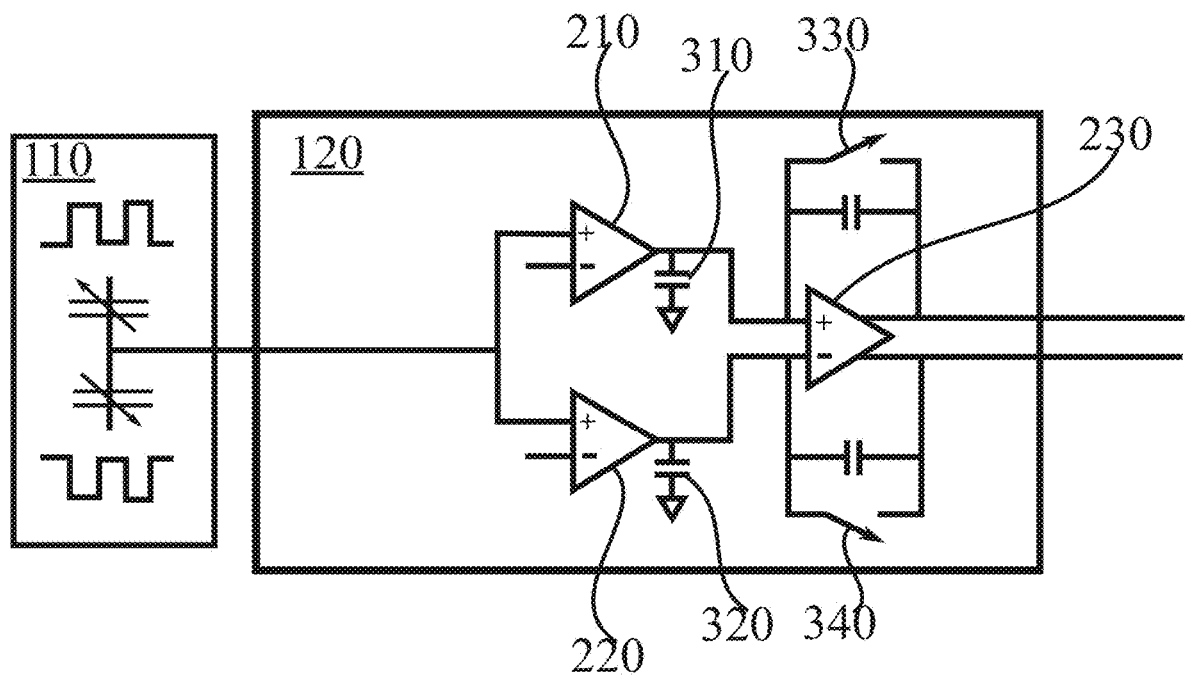
FIG. 3 illustrates an example apparatus in accordance with at least some embodiments of the present invention.

FIG. 3 illustrates an example apparatus in accordance with at least some embodiments of the present invention. The apparatus resembles that of FIG. 2, but more structure is laid out in FIG. 3. Like numbering denotes like structure as in FIG. 1 and FIG. 2.

The apparatus of FIG. 3 includes low-pass filters 310 and 320, which, as described above, may be used to control high frequency noise. Further, the apparatus of FIG. 3 includes feedbacks over differential amplifier 230. In detail, feedbacks are arranged, as illustrated, via switches 330 and 340. These switches may comprise HF switches, for example. These switches may be connected in parallel with capacitors, as illustrated in FIG. 3.

When switches 330, 340 are in the closed state, that is, in the conducting state, an output state of differential amplifier 230 is reset. When switches 330, 340 are in the open state, that is, in the non-conducting state, off-resistance of the switches 330, 340 forms a resistive feedback over differential amplifier 230 and an active high pass filter functionality is generated, the high pass filter functionality suppressing a constant acceleration component in the sensor data from the acceleration sensor. An example of a constant acceleration component is the standard acceleration g. Together with low-pass filters 310, 320, therefore, a band-pass filter functionality is generated from the resistive feedback and low-pass filters 310, 320. The band-pass filter functionality may improve the quality of seismocardiographic procedures and determinations performed using acceleration sensor data filtered with the band-pass filter functionality.

The system of FIG. 3 may further comprise, like that of FIG. 2, a processor or processing core, and memory, which may be comprised in the processor or processing core, for example. Thus the apparatus may be enabled to operate in two modes, a motion recognition state and a measurement state, for example, under the control of the processor or processing core. A motion recognition state may comprise that heart monitoring is not active, and the apparatus waits until a determination may be made, that motion disturbances are below a threshold. Responsive to the motion disturbances being determined to be below the threshold, the apparatus may switch itself to a measurement state, where heart monitoring is active. Where heart monitoring is done when motion disturbances are below a threshold, a benefit is obtained in that the acceleration sensor data is less noisy and seismocardiographic procedures may proceed with a cleaner signal. In the motion recognition state, a gain factor of the apparatus may be different, for example lower, than in the measurement state.

Figure 4:
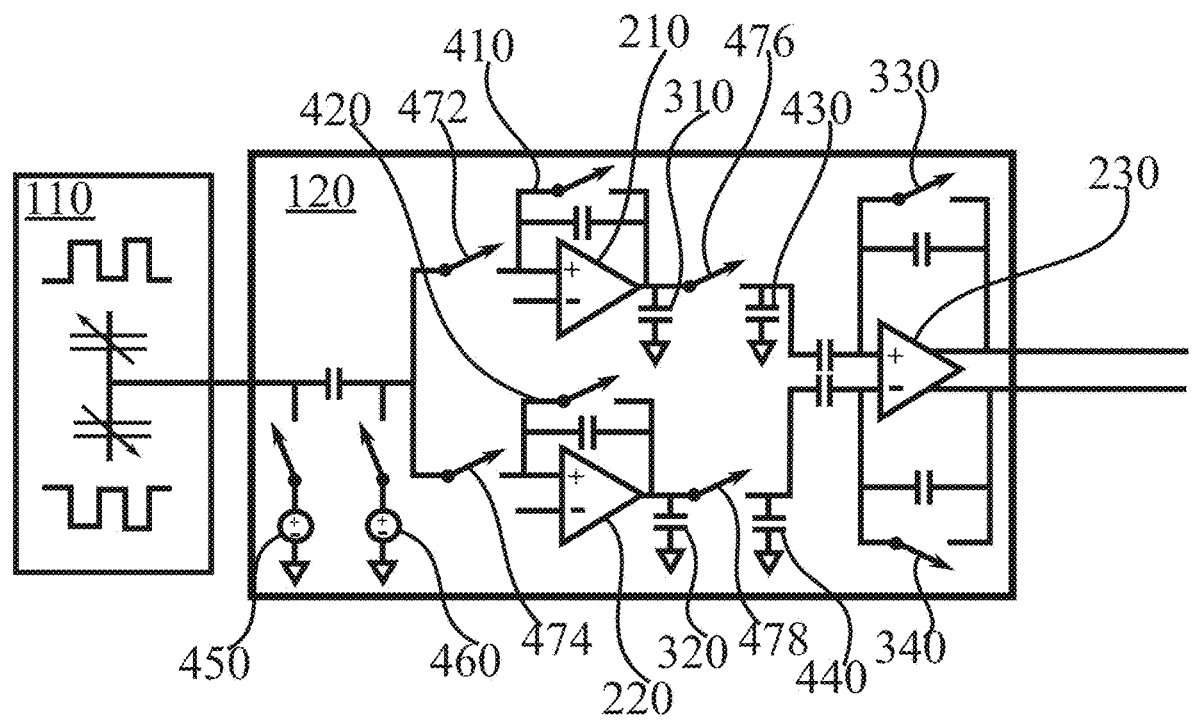
FIG. 4 illustrates an example apparatus in accordance with at least some embodiments of the present invention.

FIG. 4 illustrates an example apparatus in accordance with at least some embodiments of the present invention. The apparatus resembles that of FIG. 2 and FIG. 3, but more structure is laid out in FIG. 4. Like numbering denotes like structure as in FIG. 1, FIG. 2 and FIG. 3.

In addition to structure present in FIG. 3, FIG. 4 further illustrates hold capacitors 430 and 440. Further feedbacks 410, 420, with switches, are provided over charge amplifiers 210, 220, respectively, as illustrated. As illustrated, these switches may be connected in parallel with capacitors. Switchable voltage source 460 may be used to generate the (−) inputs for charge amplifiers 210 and 220. Switches 472 and 474 may be employed to select a negative or positive channel to read a negative and positive charge impulse. Switches 476 and 478 may be employed to charge hold capacitors 430 and 440, respectively.

In an integration phase positive and/or negative charge impulses may be converted into the voltage domain and accumulated into the feedback circuit of the positive and/or negative channel charge amplifier, respectively. Before every positive and/or negative charge impulse the input capacitor, disposed between voltage sources 450 and 460, as illustrated, may be reset into some potential by voltage sources 450 and 460 through switches. Voltage source switches turns to non-conducting state and the positive or negative channel may chosen by channel selection switches 472, 474. In the integration phase the switches in the feedback circuits 410 and 420 are in the non-conducting state. Positive and/or charge impulses from sensor 110 may apply charge change into the input capacitor, which will further induce a potential change into the input of the positive and/or charge amplifier, respectively. The amplifier may amplify and store this potential change into the feedback circuit. One integration cycle may include, for example, the following steps: resetting the input capacitor, reading and storing a positive charge impulse, resetting the input capacitor, reading and storing a negative charge impulse. During the integration phase, the feedback switches of the differential amplifier 330 and 340 are in the conducting position, thus differential amplifier is in reset mode.

After N integration cycles the sample phase may begin and the differential amplifier may exit the reset mode, namely feedback switches 330 and 340 may turn into their non-conducting positions. A cumulative voltage representing of the acceleration may be conducted to the hold capacitors 430 and 440 through sampling switches 476, 478. Differential amplifier 230 may further amplify the difference of complementary voltage signal stored into the hold capacitors 430 and 440. Sampling switches 476, 478 may then turn into their non-conducting states and feedback switches of the charge amplifiers 410 and 420 turn into their conducting positions, resetting the charge amplifiers 210, 220. A differential signal at the output of differential amplifier 230 may be further amplified, filtered or converted into the digital domain by some other devices, which are not illustrated in FIG. 4. After the sampling phase, the feedback switches of the differential amplifier 330 and 340 may be turned into their conducting positions, resetting the differential amplifier through the next integration phase.

Charge amplifiers 210, 220 may be biased to a same voltage as voltage source 460. In some embodiments, actuator signals of acceleration sensor 110 lie between voltages of voltage sources 450, 460, for example midway between these voltages. For example, if the charge amplifiers are biased at 600 mV, voltage source 460 may also be at 600 mV, and if voltage source 450 is biased to 200 mV, the actuator signal from acceleration sensor 110 is preferably, in these embodiments, 400 mV.

The system of FIG. 4 may further comprise, like that of FIG. 2 or FIG. 3, a processor or processing core, and memory, which may be comprised in the processor or processing core, for example. Thus the apparatus may be enabled to operate in two modes, a motion recognition state and a measurement state, for example, under the control of the processor or processing core. A motion recognition state may comprise that heart monitoring is not active, and the apparatus waits until a determination may be made, that motion disturbances are below a threshold. Responsive to the motion disturbances being determined to be below the threshold, the apparatus may switch itself to a measurement state, where heart monitoring is active. Where heart monitoring is done when motion disturbances are below a threshold, a benefit is obtained in that the acceleration sensor data is less noisy and seismocardiographic procedures may proceed with a cleaner signal. In the motion recognition state, a gain factor of the apparatus may be different, for example lower, than in the measurement state. Energy harvesting methods may be employed to power the system of FIG. 4, or parts thereof, or, indeed, the system of FIG. 2 or 3, or parts thereof. III-V semiconductors and/or techniques may enable very low power consumption.

In general, employing the measurement state when motion disturbances are below the threshold may reduce the amount of memory used to store, and handle, data originating in acceleration sensor 110. This is so, since data that is not useful in performing determinations concerning heart activity is not stored and may be discarded. Where the apparatus can be built with less memory, the reduced amount of memory inherently reduces power consumption of the apparatus. Also the size of the apparatus is easier to minimize when it comprises less memory. In at least some embodiments, heart monitoring is not done when the apparatus is not in the measurement state, for example, when the apparatus is in the motion recognition state. Likewise power consumption of the apparatus is reduced by limiting active heart monitoring to times when motion disturbances are below the threshold. For example, an ADC may be powered off when measurements are not recorded and where the motion recognition state may be run using analogue signals. Reduced power consumption yields increased use times when the apparatuses are battery powered. In general, responsive to motion disturbances exceeding the threshold when the measurement state is active, the apparatus is configured to interrupt the measurement state and transition to the motion recognition state.

Apparatuses according to FIG. 2, FIG. 3 and/or FIG. 4 may be employed to determine as state of the person's heart using seismocardiography, by analysing acceleration sensor data obtained from acceleration sensor 110, as processed in readout apparatus 120. For example, an atrial fibrillation state may be determined from the processed acceleration sensor data, for example by comparing the processed acceleration sensor data to a set of reference sensor data vectors, to determine a closest match reference sensor data vector that most resembles the processed acceleration sensor data obtained, via acceleration sensor 110 and readout apparatus 120, from the person. The closest match reference sensor data vector may be determined based on the least squares method or the Nelder-Mead method, for example. In case the closest match reference sensor data vector is an atrial fibrillation reference vector, the person may be determined to be in an atrial fibrillation state.

Alternatively to employing reference sensor data vectors, a determination concerning a state of the heart may be based on identifying, from the processed acceleration sensor data, characteristics and comparing the identified characteristics to reference characteristics. For example, atrial fibrillation may be determined based on a set of frequency characteristics in the processed acceleration sensor data that are characteristic of atrial fibrillation.

Figure 5:
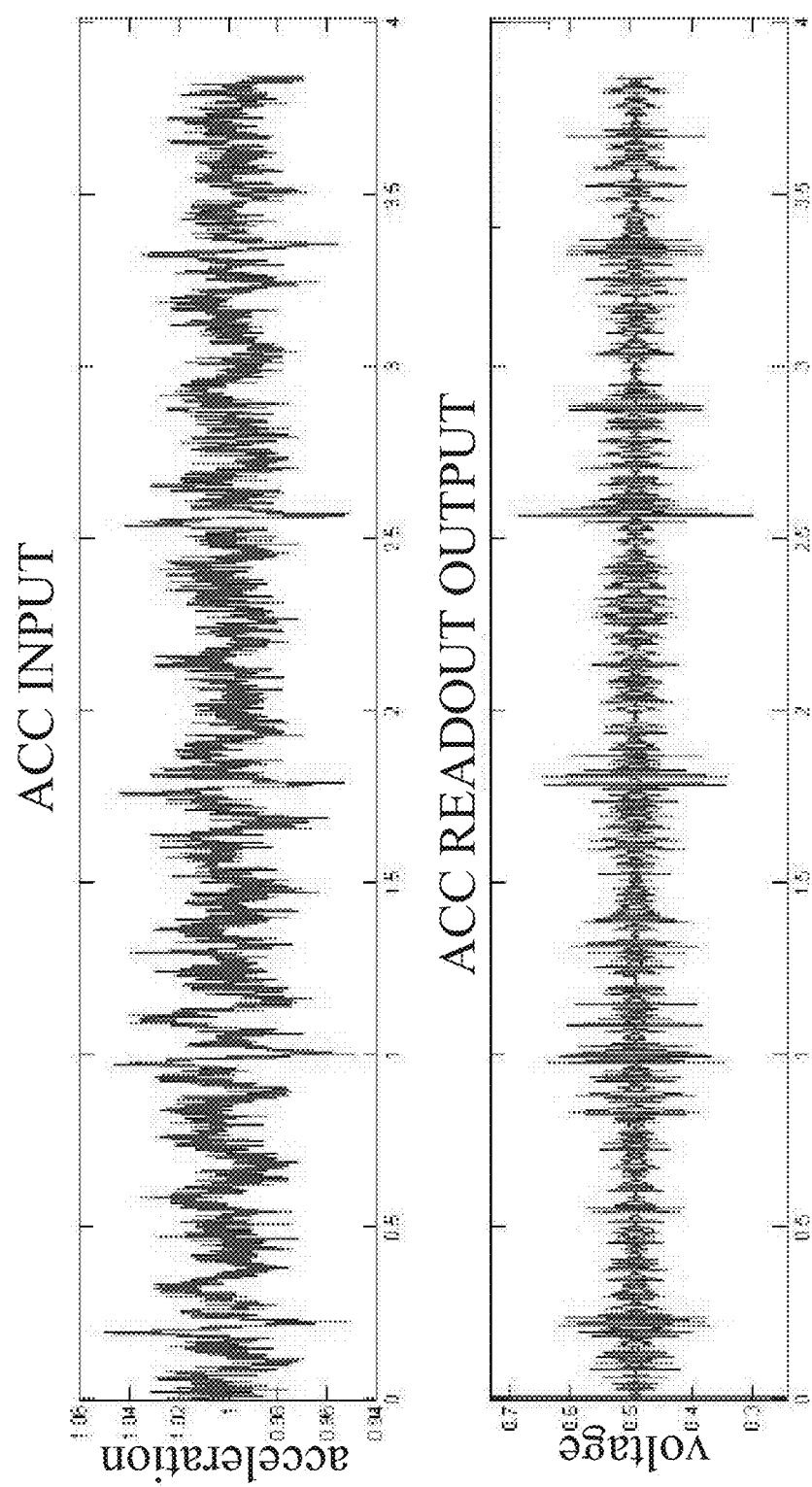
FIG. 5 illustrates filtering performed in a readout apparatus in accordance with at least some embodiments of the present invention.

FIG. 5 illustrates filtering performed in a readout apparatus in accordance with at least some embodiments of the present invention, in simulation. The ACC INPUT graph represents an output of acceleration sensor 110, which comprises the heart state information that characterizes the state of the heart, as well as various noise components. The READOUT OUTPUT graph represents an output of differential amplifier 230. The readout output signal has been processed in the readout apparatus 120, for example by filtering the one-g constant acceleration signal and amplifying.

Figure 6:
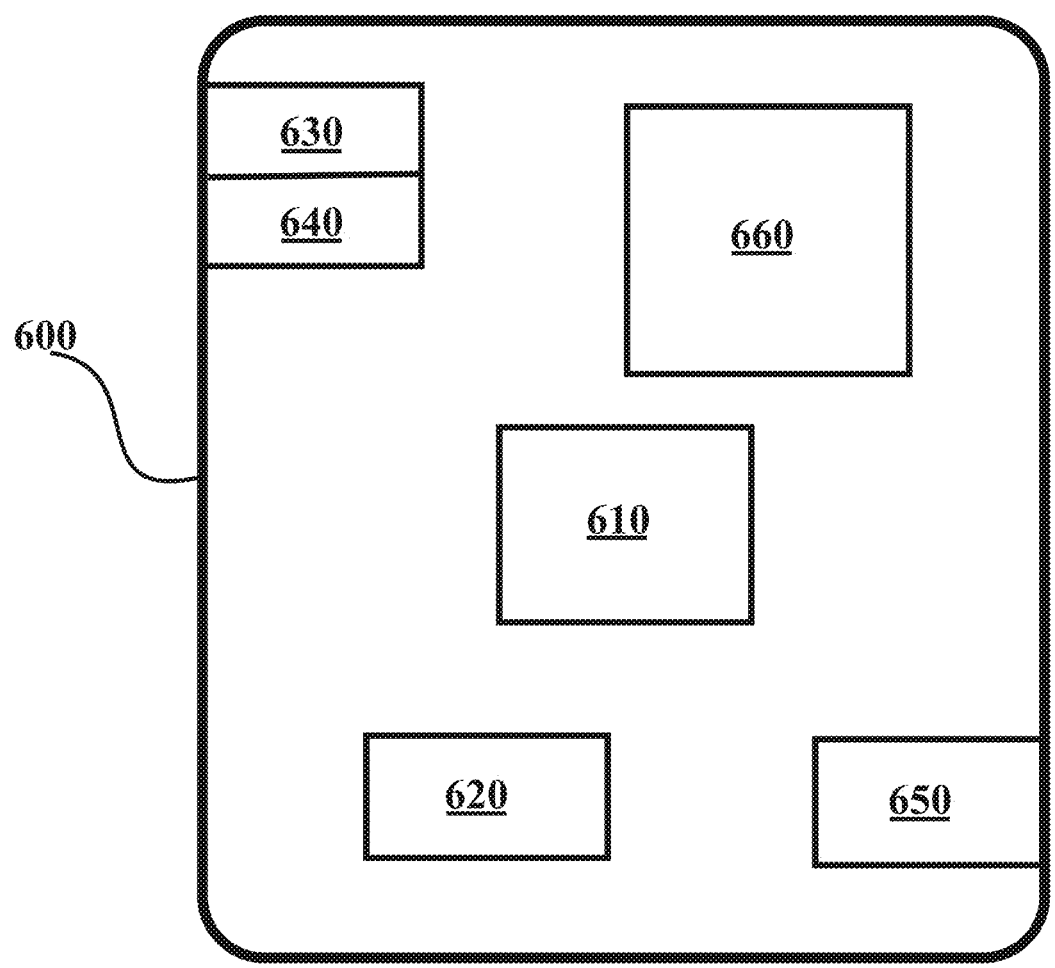
FIG. 6 illustrates an example apparatus capable of supporting at least some embodiments of the present invention.

FIG. 6 illustrates an example apparatus capable of supporting at least some embodiments of the present invention. Illustrated is device 600, which may comprise, for example, a readout apparatus or an integrated device comprising readout and analytics functions. Comprised in device 600 is processor 610, which may comprise, for example, a single- or multi-core processor wherein a single-core processor comprises one processing core and a multi-core processor comprises more than one processing core. Processor 610 may comprise more than one processor. A processing core may comprise, for example, a Cortex-A8 processing core manufactured by ARM Holdings or a Steamroller processing core produced by Advanced Micro Devices Corporation. Processor 610 may comprise at least one Qualcomm Snapdragon and/or Intel Atom processor. Processor 610 may comprise at least one application-specific integrated circuit, ASIC. Processor 610 may comprise at least one field-programmable gate array, FPGA. Processor 610 may be means for performing method steps in device 600. Processor 610 may be configured, at least in part by computer instructions, to perform actions.

Device 600 may comprise memory 620. Memory 620 may comprise random-access memory and/or permanent memory. Memory 620 may comprise at least one RAM chip. Memory 620 may comprise solid-state, magnetic, optical and/or holographic memory, for example. Memory 620 may be at least in part accessible to processor 610. Memory 620 may be at least in part comprised in processor 610. Memory 620 may be means for storing information. Memory 620 may comprise computer instructions that processor 610 is configured to execute. When computer instructions configured to cause processor 610 to perform certain actions are stored in memory 620, and device 600 overall is configured to run under the direction of processor 610 using computer instructions from memory 620, processor 610 and/or its at least one processing core may be considered to be configured to perform said certain actions. Memory 620 may be at least in part comprised in processor 610. Memory 620 may be at least in part external to device 600 but accessible to device 600.

Device 600 may comprise a transmitter 630. Device 600 may comprise a receiver 640. Transmitter 630 and receiver 640 may be configured to transmit and receive, respectively, information in accordance with at least one communication standard. Transmitter 630 may comprise more than one transmitter. Receiver 640 may comprise more than one receiver. Transmitter 630 and/or receiver 640 may be configured to operate in accordance with global system for mobile communication, GSM, wideband code division multiple access, WCDMA, 5G, long term evolution, LTE, IS-95, wireless local area network, WLAN, Ethernet and/or worldwide interoperability for microwave access, WiMAX, standards, for example.

Device 300 may comprise a readout circuitry 650. Readout circuitry 650 may comprise a readout apparatus as described herein above in connection with FIG. 2, FIG. 3 and/or FIG. 4.

Device 600 may comprise user interface, UI, 660. UI 660 may comprise at least one of a display, a keyboard, a touchscreen, a vibrator arranged to signal to a user by causing device 600 to vibrate, a speaker and a microphone. A user may be able to operate device 600 via UI 660, for example to start and stop monitoring of heart activity.

Processor 610 may be furnished with a transmitter arranged to output information from processor 610, via electrical leads internal to device 600, to other devices comprised in device 600. Such a transmitter may comprise a serial bus transmitter arranged to, for example, output information via at least one electrical lead to memory 620 for storage therein. Alternatively to a serial bus, the transmitter may comprise a parallel bus transmitter. Likewise processor 610 may comprise a receiver arranged to receive information in processor 610, via electrical leads internal to device 600, from other devices comprised in device 600. Such a receiver may comprise a serial bus receiver arranged to, for example, receive information via at least one electrical lead from receiver 640 for processing in processor 610. Alternatively to a serial bus, the receiver may comprise a parallel bus receiver.

Device 600 may comprise further devices not illustrated in FIG. 6. In some embodiments, device 600 lacks at least one device described above.

Processor 610, memory 620, transmitter 630, receiver 640, readout circuitry 650 and/or UI 660 may be interconnected by electrical leads internal to device 600 in a multitude of different ways. For example, each of the aforementioned devices may be separately connected to a master bus internal to device 600, to allow for the devices to exchange information. However, as the skilled person will appreciate, this is only one example and depending on the embodiment various ways of interconnecting at least two of the aforementioned devices may be selected without departing from the scope of the present invention.

Figure 7:
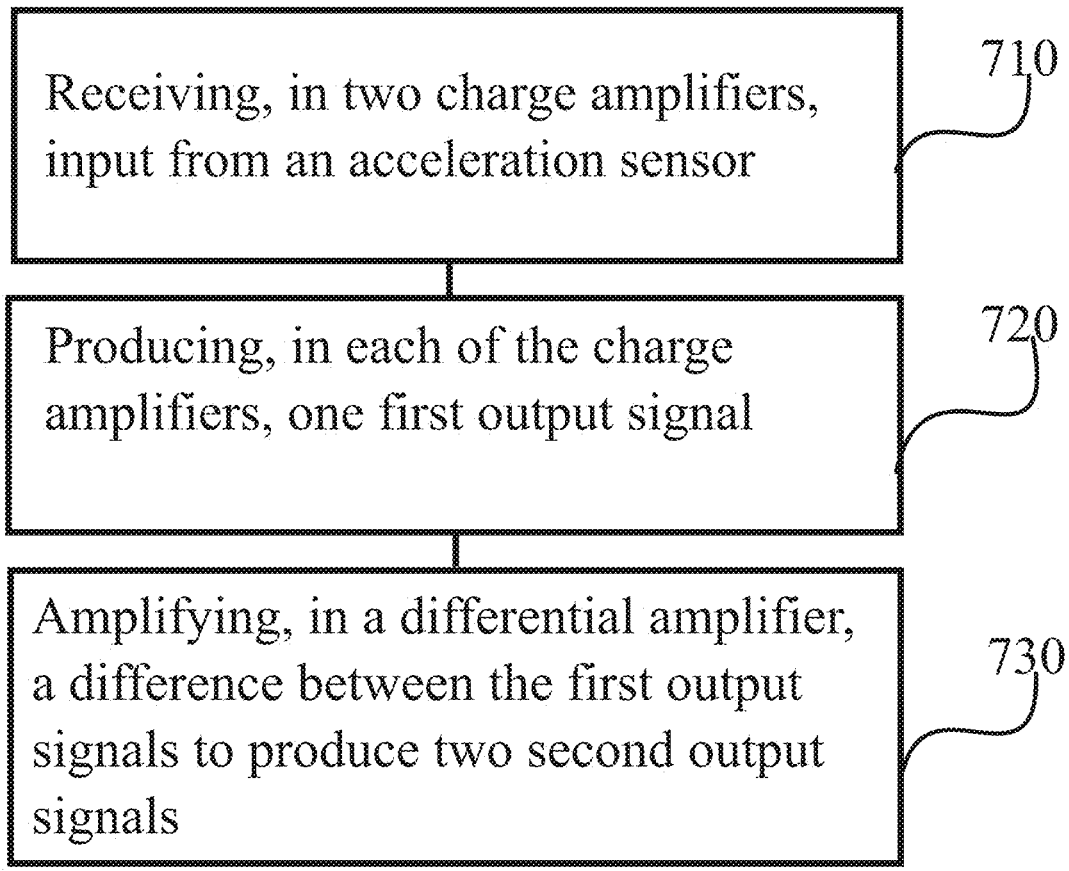
FIG. 7 is a flow graph of a method in accordance with at least some embodiments of the present invention.

FIG. 7 is a flow graph of a method in accordance with at least some embodiments of the present invention. The phases of the illustrated method may be performed in readout apparatus 120, for example.

Phase 710 comprises receiving, in two charge amplifiers, input from an acceleration sensor. Phase 720 comprises producing, in each of the charge amplifiers, one first output signal. Finally, phase 730 comprises amplifying, in a differential amplifier, a difference between the first output signals to produce two second outputs signals.

It is to be understood that the embodiments of the invention disclosed are not limited to the particular structures, process steps, or materials disclosed herein, but are extended to equivalents thereof as would be recognized by those ordinarily skilled in the relevant arts. It should also be understood that terminology employed herein is used for the purpose of describing particular embodiments only and is not intended to be limiting.

Reference throughout this specification to one embodiment or an embodiment means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment. Where reference is made to a numerical value using a term such as, for example, about or substantially, the exact numerical value is also disclosed.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present invention may be referred to herein along with alternatives for the various components thereof. It is understood that such embodiments, examples, and alternatives are not to be construed as de facto equivalents of one another, but are to be considered as separate and autonomous representations of the present invention.

Furthermore, the described features, structures, or characteristics may be combined in any suitable manner in one or more embodiments. In the preceding description, numerous specific details are provided, such as examples of lengths, widths, shapes, etc., to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The verbs "to comprise" and "to include" are used in this document as open limitations that neither exclude nor require the existence of also un-recited features. The features recited in depending claims are mutually freely combinable unless otherwise explicitly stated. Furthermore, it is to be understood that the use of "a" or "an", that is, a singular form, throughout this document does not exclude a plurality.

INDUSTRIAL APPLICABILITY

At least some embodiments of the present invention find industrial application in processing acceleration sensor data, for example for heart monitoring.

ACRONYMS LIST

ADC analogue-to-digital converter
ECG electrocardiography

| REFERENCE SIGNS LIST | |
|---|---|
| 101 | Chest |
| 110 | Acceleration sensor |
| 120 | Readout apparatus |
| 130 | Analytics device |
| 112, 123 | Connections |
| 140 | Graph |
| 210, 220 | Charge amplifier |
| 230 | Differential amplifier |
| 310, 320 | Low-pass filter |
| 330, 340 | Switch (in feedback over differential amplifier 230) |
| 410, 420 | Feedback over charge amplifier |
| 430, 440 | Hold capacitor |
| 450, 460 | Switchable voltage source |
| 472, 474, 476, 478 | Switches (FIG. 4) |
| 600 | Apparatus of FIG. 6 |
| 610-660 | Structure of the apparatus of FIG. 6 |
| 710-730 | Phases of the method of FIG. 7 |

The invention claimed is:

1. A seismocardiographic readout apparatus, comprising:
two charge amplifiers configured to receive input from an acceleration sensor and to each produce one first output signal, the acceleration sensor comprising two mechanical capacitors connected in series, the mechanical capacitors changing their capacitance according to acceleration pulses, two feedbacks being connected in the readout apparatus over a differential amplifier via respective switches, and
the differential amplifier being configured to receive the first output signals and to amplify a difference between the first output signals to produce two second output signals,
wherein when the switches are open, off-resistance of the switches forms a resistive feedback and an active high pass filter functionality is generated, the active high pass filter functionality suppressing a constant acceleration component in the input from the acceleration sensor.

2. The apparatus according to claim 1, wherein when the switches are closed, an output state of the differential amplifier is reset.

3. The apparatus according to claim 1, wherein the switches are connected in parallel with capacitors.

4. The apparatus according to claim 1, further comprising at least one processing core configured to trigger a measurement state responsive to a determination that motion disturbances are below a threshold.

5. The apparatus according to claim 4, wherein the at least one processing core is configured to maintain the apparatus in a motion recognition state when the motion disturbances are not below the threshold.

6. The apparatus according to claim 4, wherein the at least one processing core is configured to, based on the second output signals, determine whether a person the acceleration sensor is measuring is experiencing atrial fibrillation.

7. The apparatus according to claim 1, further comprising a differential analogue to digital converter configured to receive the two second output signals, and to output a digital representation thereof.

8. A method, comprising:
receiving, in two charge amplifiers, input from an acceleration sensor, the acceleration sensor comprising two mechanical capacitors connected in series, the mechanical capacitors changing their capacitance according to acceleration pulses, two feedbacks being connected over a differential amplifier via respective switches;
producing, in each of the charge amplifiers, one first output signal, and
amplifying, in the differential amplifier, a difference between the first output signals to produce two second output signals,
wherein when the switches are open, off-resistance of the switches forms a resistive feedback and an active high pass filter functionality is generated, the active high pass filter functionality suppressing a constant acceleration component in the input from the acceleration sensor.

9. The method according to claim 8, further comprising resetting an output state of the differential amplifier by closing the switches.

10. The method according to claim 8, wherein the switches are connected in parallel with capacitors.

11. The method according to claim 8, further comprising triggering, by at least one processing core, a measurement state responsive to a determination that motion disturbances are below a threshold.

12. The method according to claim 11, further comprising maintaining, by the at least one processing core, a motion recognition state when the motion disturbances are not below the threshold.

13. The method according to claim 11, further comprising determining, by the at least one processing core, based on the second output signals, whether a person the acceleration sensor is measuring is experiencing atrial fibrillation.

14. The method according to claim 8, further comprising receiving the two second output signals in a differential analogue to digital converter, and outputting a digital representation thereof.

15. A non-transitory computer readable medium, having stored thereon a set of computer readable instructions that, when executed by at least one processor, cause an apparatus to at least:

receive, in two charge amplifiers, input from an acceleration sensor, the acceleration sensor comprising two mechanical capacitors connected in series, the mechanical capacitors changing their capacitance according to acceleration pulses, two feedbacks being connected in the apparatus over a differential amplifier via respective switches;

produce, in each of the charge amplifiers, one first output signal, and amplify, in the differential amplifier, a difference between the first output signals to produce two second output signals, wherein when the switches are open, off-resistance of the switches forms a resistive feedback and an active high pass filter functionality is generated, the active high pass filter functionality suppressing a constant acceleration component in the input from the acceleration sensor.

* * * * *